(12) United States Patent
Vongnam et al.

(10) Patent No.: US 12,377,406 B2
(45) Date of Patent: Aug. 5, 2025

(54) CATALYST COMPOSITION FOR CYCLIC CARBONATE PRODUCTION FROM $CO_2$ AND OLEFINS

(71) Applicant: PTT GLOBAL CHEMICAL PUBLIC COMPANY LIMITED, Chatuchak (TH)

(72) Inventors: Kunnigar Vongnam, Nonsang (TH); Nopparat Thavornsin, Pakkred (TH); Pornpen Sae-Ung, Muangnakornpathom (TH); Sophon Kaeothip, Chatuchak (TH); Anucha Euapermkiati, Chatuchak (TH); Khamphee Phomphrai, Buengkum (TH)

(73) Assignee: PTT GLOBAL CHEMICAL PUBLIC COMPANY LIMITED, Chatuchak (TH)

( * ) Notice: Subject to any disclaimer, the term of this patent is extended or adjusted under 35 U.S.C. 154(b) by 759 days.

(21) Appl. No.: 17/764,400

(22) PCT Filed: Sep. 30, 2020

(86) PCT No.: PCT/TH2020/000066
§ 371 (c)(1),
(2) Date: Mar. 28, 2022

(87) PCT Pub. No.: WO2021/066756
PCT Pub. Date: Apr. 8, 2021

(65) Prior Publication Data
US 2022/0401937 A1 Dec. 22, 2022

(30) Foreign Application Priority Data

Sep. 30, 2019 (TH) .................................. 1901006270

(51) Int. Cl.
*B01J 31/22* (2006.01)
*C07D 317/38* (2006.01)
(52) U.S. Cl.
CPC ........ *B01J 31/2243* (2013.01); *C07D 317/38* (2013.01); *B01J 2231/70* (2013.01)
(58) Field of Classification Search
CPC .................................................. B01J 31/2243
See application file for complete search history.

(56) References Cited

U.S. PATENT DOCUMENTS

2014/0066533 A1    3/2014    Deng et al.

FOREIGN PATENT DOCUMENTS

| CN | 101045767 A | 10/2007 |
|---|---|---|
| CN | 101245117 A | 8/2008 |
| CN | 100549043 C | 10/2009 |
| WO | 2008034265 A1 | 3/2008 |
| WO | 2013022932 A1 | 2/2013 |
| WO | 2014204279 A1 | 12/2014 |

OTHER PUBLICATIONS

Huang et al., "Half-Sandwich Chromium (III) Catalysts Bearing Hydroxyindanimine Ligands for Ethylene Polymerization", ORGANOMETALLICS, vol. 28, No. 14, Jun. 18, 2009, pp. 4170-4174.
Extended European Search Report for EP Application No. 20870651, mailed Oct. 23, 2023, 1 p.
International Search Report in International Patent Application No. PCT/TH2020/000066 mailed Apr. 28, 2021 (3 pp.).
Written Opinion in International Patent Application No. PCT/TH2020/000066 mailed Apr. 28, 2021 (4 pp.).

*Primary Examiner* — Golam M Shameem
(74) *Attorney, Agent, or Firm* — NIXON PEABODY LLP

(57) ABSTRACT

The present invention relates to catalyst composition for cyclic carbonate production from $CO_2$ and olefins using halohydrin agent as the co-reactant under mild conditions, which can effectively catalyze the cyclic carbonate synthesis and provides good selectivity to cyclic carbonate, wherein said catalyst composition comprising:
a) the metal complex as shown in structure (I):

wherein,
M represents transition metal atom;
$R_1$, $R_2$, and $R_3$ represent independent group selected from hydrogen atom, halogen atom, alkyl group, alkenyl group, alkynyl group, alkoxy group, amine group, phenyl group, benzyl group, cyclic hydrocarbon group comprising hetero atom, perfluoroalkyl group, or nitro group;
$R_4$ represents group selected from alkylene group, cycloalkylene group, or phenylene group;
X represents group selected from halogen atom, acetate group, or triflate group;
b) the halohydrin agent in at least one solvent; and
c) at least one base.

18 Claims, No Drawings

CATALYST COMPOSITION FOR CYCLIC CARBONATE PRODUCTION FROM $CO_2$ AND OLEFINS

CROSS-REFERENCE TO RELATED APPLICATIONS

This application is the United States National Phase of International Application No.: PCT/TH2020/000066, filed Sep. 30, 2020, which in turn claims priority benefit of Thailand Application No.: 1901006270, filed Sep. 30, 2019, the entire contents of which are herein incorporated by reference in their entirety.

TECHNICAL FIELD

The present invention relates to the field of science, in particular, to the catalyst composition for cyclic carbonate production from $CO_2$ and olefins.

BACKGROUND ART

Cyclic carbonate is the valuable chemical and is very important in both chemical and polymer industry. In chemical industry, cyclic carbonate is popularly used as the polar aprotic solvent in which the cyclic carbonates popularly used are ethylene carbonate and propylene carbonate. They are used instead of the polar aprotic solvents such as dimethylformamide, hexamethylphosphoramide, N-methyl-2-pyrrolidone, dimethylacetamide, etc. This is because the cyclic carbonate has low toxicity, low vapour pressure, high flash point, and it is more environmental friendly. Moreover, in downstream chemical industry such as dye, medicine, and cosmetic, the cyclic carbonate is regarded as the medium popularly used for the production or synthesis of these downstream chemicals, especially in the personal care products.

In polymer industry, the cyclic carbonate is the important precursor for the production of polymers that are polycarbonates and polyurethanes, including polycarbonate diols (PCDLs) used in the production of polyurethane that requires special properties in terms of better elasticity and mechanical properties, durability to weather conditions and fungi, and resistance to oxidation and protection from ultraviolet ray. Meanwhile, the cyclic carbonate is also the important substance used in the production of important chemicals in polymer industry such as 1,4-bis(2-hydroxyethoxy)benzene (HQEE) synthesized from ethylene carbonate to be used as the spacer in the production of polyurethane having property that resists to chemicals and heat and high strength for using in vehicle tire production, or 1,3,5-tris(2-hydroxyethyl)isocyanurate (THEIC) synthesized from ethylene carbonate to be used as the cross-linking agent for the production of polyethylene resin having property that resists to corrosion that is suitable for covering electrical cables. Apart from the use of the cyclic carbonate in the production of chemicals in the polymer industry, the cyclic carbonate is also popularly used to be added into polymer directly in order to improve polymer properties.

For the synthesis of such cyclic carbonate, the phosgene could be formerly used as precursor in the synthesis such as the synthesis of ethylene carbonate from phosgene and ethylene glycol. However, said synthesis process is quite dangerous and affects the environment because phosgene has high toxicity. Therefore, the synthesis process of the cyclic carbonate from other precursors instead of phosgene had been developed. At present, the carbon source, which has gained interests in using as the precursor in the production of valuable chemicals including fuel, is carbon dioxide which is the important C1 building block due to low toxicity, low cost, and the ability in reuse of renewable resource. Therefore, the carbon dioxide has been used as the precursor in the synthesis of the cyclic carbonate, especially in the synthesis of cyclic carbonate from the reaction between carbon dioxide and epoxides which had been disclosed firstly in the patent document DE 740,366. The advantage of this synthesis process is that the reaction has 100% atom efficiency of chemical process conversion. That means all atoms of precursor are changed to the product, making the synthesis process via this reaction to be efficient in capturing and storing carbon dioxide in the form of cyclic carbonate product.

Nevertheless, most epoxides are made from olefins. Therefore, there have been development and invention of the production process of cyclic carbonate using olefins as the precursor together with carbon dioxide instead of using epoxides as the precursor together with carbon dioxide in order to reduce the production step of epoxides from olefins and the separation step of epoxides from said process for further using in cyclic carbonate production. The production process of the cyclic carbonate from olefins and carbon dioxide is interesting because the precursor used in this process has low cost, is easy to find, and has less toxicity when comparing to the production process using epoxides as the precursor. The production process of the cyclic carbonate from olefins and carbon dioxide can be divided into 2 features as follows:

The first feature is the oxidative carboxylation reaction, wherein the precursor which is olefins reacts with the oxidant to form the epoxides via epoxidation in the first step before reacting with carbon dioxide to form the cyclic carbonate via carboxylation. Example is the disclosure of the production of the cyclic carbonate in the patent document U.S. Pat. No. 3,025,305 in which said disclosed process is the reaction between olefins with carbon dioxide at the pressure at least 500 psig and gas in which molecule has oxygen as composition at operating temperature of 200 to 400° F. and using catalyst system comprising cobalt organic salt oxidation catalyst and the co-catalyst which is the quaternary ammonium compound. However, this production of cyclic carbonate has disadvantage that provides low selectivity and yield of the cyclic carbonate because the first step in which olefins react with the oxidant gives oxidative by-products such as benzaldehyde and benzoic acid, apart from epoxides. This results in lower yield of epoxides produced and causes lower yield of the cyclic carbonate too.

The second feature is the hydroxyhalogenation-carboxylation reaction, wherein the precursor which is olefins reacts with the halohydrin reagent such as N-bromosuccinimide (NBS) or bromide ion/hydrogen peroxide ($Br^-/H_2O_2$) via hydroxyhalogenation in the first step to from the intermediate which is halohydrin before reacting with carbon dioxide to form the cyclic carbonate via carboxylation. This feature of the production of the cyclic carbonate has better efficiency then the first feature wherein the production process of the cyclic carbonate via hydroxyhalogenation-carboxylation and the halohydrin synthesis from olefins have been disclosed in the following documents.

Patent document U.S. Pat. No. 3,884,984 discloses the synthesis process of the halohydrin such as chlorohydrin or bromohydrin by the reaction between olefins such as ethylene with water and ion of chlorine or bromine under the presence of thallium salt. While patent document U.S. Pat.

No. 3,923,842 discloses the production process of the cyclic carbonate having 3 to 31 carbon atoms by the reaction between the halohydrin and carbon dioxide under the presence of amine compound.

Patent document U.S. Pat. No. 4,325,874 discloses the production process of alkylene carbonates such as ethylene carbonate by the reaction between olefins and carbon dioxide under the presence of iodine or iodine compound and thallium oxide compound or salt which is weak acid of thallium.

Patent document WO 2008/034265 A1 discloses the production process of cyclic carbonate in aqueous from alkene and carbon dioxide via intermediate in the form of halohydrin such as bromohydrin. The cyclic carbonate production disclosed in this document is the reaction in aqueous between alkene and carbon dioxide under the presence of halogen compound and base having amine group, or the reaction in aqueous between alkene and carbon dioxide under the presence of halogen compound, base having amine group, and oxidant. The example of halogen compounds are N-bromosuccinimide (NBS), tetrabutylammonium bromide (TBAB), potassium bromide (KBr), or sodium bromide (NaBr), etc. The example of base having amine group is 1,8-diazabicyclo[5.4.0]undec-7-ene (DBU), etc. The example of oxidant is hydrogen peroxide ($H_2O_2$), etc. It was found that this production process can be effectively operated under mild conditions.

Jia-Ning Xie et al. (Journal of $CO_2$ Utilization, 2016, 16, 313-317) discloses the direct synthesis of the cyclic carbonate from olefins and carbon dioxide under mild conditions that is carbon dioxide pressure of 3 MPa and temperature at 60° C. Potassium peroxodisulfate ($K_2S_2O_8$) was used as an oxidant and sodium bromide (NaBr) was used as the bromination reagent for the early stage of hydroxyhalogenation of olefins. Then, it was reacted with carbon dioxide to form the cyclic carbonate via carboxylation using potassium carbonate ($K_2CO_3$) as the deprotonation reagent together with polyethylene glycol (PEG). It was found that under said operating conditions, this process can produce cyclic carbonate. However, the use of polyethylene glycol in said production process has disadvantage in the term of separation of the cyclic carbonate product and polyethylene glycol. Moreover, this synthesis process also takes long operating time.

Therefore, the present invention aims to prepare the catalyst composition for cyclic carbonate production from $CO_2$ and olefins using halohydrin agent as the co-reactant under mild conditions, wherein the synthesis of cyclic carbonate can be efficiently catalyzed with good selectivity to cyclic carbonate.

SUMMARY OF INVENTION

The present invention relates to catalyst composition for cyclic carbonate production from $CO_2$ and olefins using halohydrin agent as the co-reactant under mild conditions, which can effectively catalyze the cyclic carbonate synthesis and provides good selectivity to cyclic carbonate, wherein said catalyst composition comprising:

a) the metal complex as shown in structure (I):

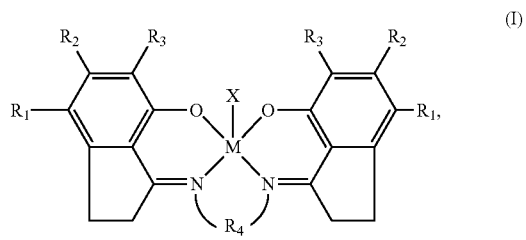

wherein,
M represents transition metal atom;
$R_1$, $R_2$, and $R_3$ represent independent group selected from hydrogen atom, halogen atom, alkyl group, alkenyl group, alkynyl group, alkoxy group, amine group, phenyl group, benzyl group, cyclic hydrocarbon group comprising hetero atom, perfluoroalkyl group, or nitro group;
$R_4$ represents group selected from alkylene group, cycloalkylene group, or phenylene group;
X represents group selected from halogen atom, acetate group, or triflate group;
b) the halohydrin agent in at least one solvent; and
c) at least one base.

DESCRIPTION OF THE INVENTION

The present invention relates to the catalyst composition for cyclic carbonate production from $CO_2$ and olefins under mild conditions, wherein the catalyst according to the invention can efficiently catalyze the synthesis of cyclic carbonate with good selectivity to cyclic carbonate, wherein the catalyst according to the invention can be described according to the following embodiments.

Any aspect being described herein also means to include the application to other aspects of this invention unless stated otherwise.

Technical terms or scientific terms used herein have definitions as understood by an ordinary person skilled in the art unless stated otherwise.

Any tools, equipment, methods, or chemicals named herein mean tools, equipment, methods, or chemicals being operated or used commonly by those person skilled in the art unless stated otherwise that they are tools, equipment, methods, or chemicals specific only in this invention.

Use of singular noun or singular pronoun with "comprising" in claims or specification means "one" and also including "one or more", "at least one", and "one or more than one".

All compositions and/or methods disclosed and claims in this application are intended to cover embodiments from any operation, performance, modification, or adjustment any factors without any experiment that significantly different from this invention, and obtain with object with utility and resulted as same as the present embodiment according to person ordinary skilled in the art although without specifically stated in claims. Therefore, substitutable or similar object to the present embodiment, including any minor modification or adjustment that can be apparent to person skilled in the art should be construed as remains in spirit, scope, and concept of invention as appeared in appended claims.

Throughout this application, term "about" means any number that appeared or expressed herein that could be varied or deviated from any error of equipment, method, or personal using said equipment or method.

Hereafter, invention embodiments are shown without any purpose to limit any scope of the invention.

This invention relates to the catalyst composition for cyclic carbonate production from $CO_2$ and olefins using halohydrin agent as the co-reactant under mild conditions, which can efficiently catalyze the cyclic carbonate synthesis with good selectivity to cyclic carbonate, wherein said catalyst composition comprising:

a) the metal complex as shown in structure (I):

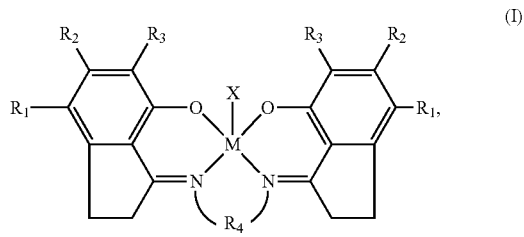

wherein,

M represents transition metal atom;

$R_1$, $R_2$, and $R_3$ represent independent group selected from hydrogen atom, halogen atom, alkyl group, alkenyl group, alkynyl group, alkoxy group, amine group, phenyl group, benzyl group, cyclic hydrocarbon group comprising hetero atom, perfluoroalkyl group, or nitro group;

$R_4$ represents group selected from alkylene group, cycloalkylene group, or phenylene group;

X represents group selected from halogen atom, acetate group, or triflate group;

b) the halohydrin agent in at least one solvent; and c) at least one base.

Preferably, in the metal complex in a), M represents transition metal atom selected from chromium, cobalt, or iron. More preferably, M is chromium metal atom.

In one aspect of the invention, in the metal complex in a), $R_1$, $R_2$, and $R_3$ represent independent group selected from hydrogen atom, halogen atom, alkyl group having 1 to 4 carbon atoms, alkenyl group having 1 to 4 carbon atoms, alkynyl group having 1 to 4 carbon atoms, alkoxy group having 1 to 4 carbon atoms, amine group, phenyl group, benzyl group, cyclic hydrocarbon group comprising hetero atom, perfluoroalkyl group, or nitro group.

In one aspect of the invention, in the metal complex in a), $R_1$, $R_2$, and $R_3$ represent independent group selected from, but not limited to hydrogen atom, chlorine atom, methyl group, ethyl group, iso-propyl group, n-butyl group, tert-butyl group, methoxy group, ethoxy group, iso-propoxy group, n-butoxy group, tert-butoxy group, phenyl group, benzyl group, trifluoromethyl group, or nitro group. Preferably, in the metal complex in a), $R_1$, $R_2$, and $R_3$ are hydrogen atom.

In one aspect of the invention, in the metal complex in a), $R_4$ represents group selected from alkylene group having 2 to 3 carbon atoms, cycloalkylene group having 6 carbon atoms, or phenylene group.

In one aspect of the invention, in the metal complex in a), $R_4$ represents group selected from, but not limited to ethylene group, 1,3-propylene group, 1,2-cyclohexylene group, or 1,2-phenylene group. Preferably, in the metal complex in a), $R_4$ represents group selected from 1,2-phenylene group.

In one aspect of the invention, in the metal complex in a), X represents group selected from, but not limited to chlorine atom, bromine atom, iodine atom, acetate group, or triflate group.

In one aspect of the invention, the metal complex in a) is selected from N—N'-bis(ethylenesalicylidene)-ethane-1,2-diamino metal (III) chloride, N—N'-bis(ethylenesalicylidene)-propane-1,3-diamino metal (III) chloride, N—N'-bis(ethylenesalicylidene)-benzene-1,2-diamino metal (III) chloride, N—N'-bis(ethylenesalicylidene)-cyclohexane-1,2-diamino metal (III) chloride, N—N'-bis(3,5-di-tert-butyl ethylenesalicylidene)-ethane-1,2-diamino metal (III) chloride, N—N'-bis(3,5-di-methyl ethylenesalicylidene)-ethane-1,2-diamino metal (III) chloride, N—N'-bis(3-methyl ethylenesalicylidene)-ethane-1,2-diamino metal (III) chloride, N—N'-bis(5-methyl ethylenesalicylidene)-ethane-1,2-diamino metal (III) chloride, N—N'-bis(3-tert-butyl ethylenesalicylidene)-ethane-1,2-diamino metal (III) chloride, N—N'-bis(5-tert-butyl ethylenesalicylidene)-ethane-1,2-diamino metal (III) chloride, N—N'-bis(3-methyl, 5-tert-butyl ethylenesalicylidene)-ethane-1,2-diamino metal (III) chloride, N—N'-bis(3-tert-butyl, 5-methyl ethylenesalicylidene)-ethane-1,2-diamino metal (III) chloride, N—N'-bis(3-tert-butyl, 5-trifluoromethyl ethylenesalicylidene)-ethane-1,2-diamino metal (III) chloride, N—N'-bis(3-tert-butyl, 5-methoxy ethylenesalicylidene)-ethane-1,2-diamino metal (III) chloride, N—N'-bis(3-tert-butyl, 5-nitro ethylenesalicylidene)-ethane-1,2-diamino metal (III) chloride, N—N'-bis(3-tert-butyl, 5-chloro ethylenesalicylidene)-ethane-1,2-diamino metal (III) chloride, N—N'-bis(3-methyl, 5-trifluoromethyl ethylenesalicylidene)-ethane-1,2-diamino metal (III) chloride, N—N'-bis(3-methyl, 5-methoxy ethylenesalicylidene)-ethane-1,2-diamino metal (III) chloride, N—N'-bis(3-methyl, 5-nitro ethylenesalicylidene)-ethane-1,2-diamino metal (III) chloride, N—N'-bis(3-methyl, 5-chloro ethylenesalicylidene)-ethane-1,2-diamino metal (III) chloride, N—N'-bis(3,5-di-tert-butyl ethylenesalicylidene)-propane-1,3-diamino metal (III) chloride, N—N'-bis(3,5-di-methyl ethylenesalicylidene)-propane-1,3-diamino metal (III) chloride, N—N'-bis(3-methyl ethylenesalicylidene)-propane-1,3-diamino metal (III) chloride, N—N'-bis(5-methyl ethylenesalicylidene)-propane-1,3-diamino metal (III) chloride, N—N'-bis(3-tert-butyl ethylenesalicylidene)-propane-1,3-diamino metal (III) chloride, N—N'-bis(5-tert-butyl ethylenesalicylidene)-propane-1,3-diamino metal (III) chloride, N—N'-bis(3-methyl, 5-tert-butyl ethylenesalicylidene)-propane-1,3-diamino metal (III) chloride, N—N'-bis(3-tert-butyl, 5-methyl ethylenesalicylidene)-propane-1,3-diamino metal (III) chloride, N—N'-bis(3-tert-butyl, 5-trifluoromethyl ethylenesalicylidene)-propane-1,3-diamino metal (III) chloride, N—N'-bis(3-tert-butyl, 5-methoxy ethylenesalicylidene)-propane-1,3-diamino metal (III) chloride, N—N'-bis(3-tert-butyl, 5-nitro ethylenesalicylidene)-propane-1,3-diamino metal (III) chloride, N—N'-bis(3-tert-butyl, 5-chloro ethylenesalicylidene)-propane-1,3-diamino metal (III) chloride, N—N'-bis(3-methyl, 5-trifluoromethyl ethylenesalicylidene)-propane-1,3-diamino metal (III) chloride, N—N'-bis(3-methyl, 5-methoxy ethylenesalicylidene)-propane-1,3-diamino metal (III) chloride, N—N'-bis(3-methyl, 5-nitro ethylenesalicylidene)-propane-1,3-diamino metal (III) chloride, N—N'-bis(3-methyl, 5-chloro ethylenesalicylidene)-propane-1,3-diamino metal (III) chloride, N—N'-bis(3,5-di-tert-butyl ethylenesalicylidene)-benzene-1,2-diamino metal (III) chloride, N—N'-bis(3,5-di-methyl ethylenesalicylidene)-benzene-1,2-diamino metal (III) chloride, N—N'-bis(3-methyl ethylenesalicylidene)-benzene-1,2-diamino metal (III) chloride, N—N'-bis(5-methyl ethylenesalicylidene)-benzene-1,2-diamino metal (III) chloride, N—N'-bis(3-tert-butyl ethylenesalicylidene)-benzene-1,2-diamino metal (III) chloride, N—N'-bis(5-tert-butyl ethylenesalicylidene)-benzene-1,2-diamino metal (III) chloride, N—N'-bis(3-methyl, 5-tert-butyl ethylenesalicylidene)-benzene-1,2-diamino metal (III) chloride, N—N'-bis(3-tert-butyl, 5-methyl ethylenesalicylidene)-benzene-1,2-diamino metal (III) chloride, N—N'-bis(3-tert-butyl, 5-trifluoromethyl ethylenesalicylidene)-benzene-1,2-diamino metal (III) chloride, N—N'-bis(3-tert-butyl, 5-methoxy ethylenesalicylidene)-benzene-1,2-diamino metal (III) chloride, N—N'-bis(3-tert-butyl, 5-nitro ethylenesalicylidene)-benzene-1,2-diamino metal (III) chloride, N—N'-bis(3-tert-butyl, 5-chloro ethylenesalicylidene)-benzene-1,2-diamino metal (III) chloride, N—N'-bis(3-methyl, 5-trifluoromethyl ethylenesalicylidene)-benzene-1,2-diamino metal (III) chloride, N—N'-bis(3-methyl, 5-methoxy ethylenesalicylidene)-benzene-1,2-diamino metal (III) chloride, N—N'-bis(3-methyl, 5-nitro ethylenesalicylidene)-benzene-1,2-diamino metal (III) chloride, N—N'-bis(3-methyl, 5-chloro ethylenesalicylidene)-benzene-1,2-diamino metal (III) chloride, N—N'-bis(3,5-di-tert-butyl ethylenesalicylidene)-cyclohexane-1,2-diamino metal (III) chloride, N—N'-bis(3,5-di-methyl ethylenesalicylidene)-cyclohexane-1,2-diamino metal (III) chloride, N—N'-bis(3-methyl ethylenesalicylidene)-cyclohexane-1,2-diamino metal (III) chloride, N—N'-bis(5-methyl ethylenesalicylidene)-cyclohexane-1,2-diamino metal (III) chloride, N—N'-bis(3-tert-butyl ethylenesalicylidene)-cyclohexane-1,2-diamino metal (III) chloride, N—N'-bis(5-tert-butyl ethylenesalicylidene)-cyclohexane-1,2-diamino metal (III) chloride, N—N'-bis(3-methyl, 5-tert-butyl ethylenesalicylidene)-cyclohexane-1,2-diamino metal (III) chloride, N—N'-bis(3-tert-butyl, 5-methyl ethylenesalicylidene)-cyclohexane-1,2-diamino metal (III) chloride, N—N'-bis(3-tert-butyl, 5-trifluoromethyl ethylenesalicylidene)-cyclohexane-1,2-diamino metal (III) chloride, N—N'-bis(3-tert-butyl, 5-methoxy ethylenesalicylidene)-cyclohexane-1,2-diamino metal (III) chloride, N—N'-bis(3-tert-butyl, 5-nitro ethylenesalicylidene)-cyclohexane-1,2-diamino metal (III) chloride, N—N'-bis(3-tert-butyl, 5-chloro ethylenesalicylidene)-cyclohexane-1,2-diamino metal (III) chloride, N—N'-bis(3-methyl, 5-trifluoromethyl ethylenesalicylidene)-cyclohexane-1,2-diamino metal (III) chloride, N—N'-bis(3-methyl, 5-methoxy ethylenesalicylidene)-cyclohexane-1,2-diamino metal (III) chloride, N—N'-bis(3-methyl, 5-nitro ethylenesalicylidene)-cyclohexane-1,2-diamino metal (III) chloride, or N—N'-bis(3-methyl, 5-chloro ethylenesalicylidene)-cyclohexane-1,2-diamino metal (III) chloride.

In one aspect of the invention, the metal complex in a) can be synthesized from the reaction between metal salt precursor and N—N'-bis(ethylenesalicylidene)-diamine ligand and its derivatives, wherein the mole ratio of the reaction between metal salt and said ligand is in the range of 1:1 to 1:2.

In one aspect of the invention, the chromium metal salt precursor for the invention of the metal complex in a) may be selected from, but not limited to chromium (III) chloride ($CrCl_3$), chromium (III) chloride tetrahydrofuran ($CrCl_3$ $(THF)_3$), chromium (II) chloride ($CrCl_2$), chromium (III) chloride hexahydrate ($CrCl_3$ $6H_2O$), chromium (III) bromide ($CrBr_3$), chromium (III) iodide ($CrI_3$), chromium (III) acetate ($Cr(C_2H_3O_2)_3$), or chromium (III) triflate ($Cr(CF_3SO_3)_3$). Preferably, the chromium metal salt precursor for the invention of the metal complex in a) is selected from chromium (III) chloride tetrahydrofuran ($CrCl_3$ $(THF)_3$) or chromium (II) chloride ($CrCl_2$).

In one aspect of the invention, the cobalt metal salt precursor for the invention of the metal complex in a) may be selected from, but not limited to cobalt (II) chloride ($CoCl_2$), cobalt (II) chloride hexahydrate ($CoCl_2$ $6H_2O$), cobalt (II) bromide ($CoBr_2$), cobalt (II) iodide ($CoI_2$), cobalt (II) acetate ($Co(CH_3CO_2)_2$), or cobalt (II) triflate ($Co(CF_3SO_3)_2$). Preferably, the cobalt metal salt precursor for the invention of the metal complex in a) is selected from cobalt (II) chloride ($CoCl_2$).

In one aspect of the invention, the iron metal salt precursor for the invention of the metal complex in a) may be selected from, but not limited to iron (III) chloride ($FeCl_3$), iron (III) chloride hexahydrate ($FeCl_3$ $6H_2O$), iron (III) bromide ($FeBr_3$), iron (III) iodide ($FeI_3$), iron (III) acetate ($Fe(C_2H_3O_2)_3$), or iron (III) triflate ($Fe(CF_3SO_3)_3$). Preferably, the iron metal salt precursor for the invention of the metal complex in a) is selected from iron (III) chloride ($FeCl_3$).

In one aspect of the invention, the N—N'-bis(ethylenesalicylidene)-diamine ligand and its derivatives is selected from, but not limited to N—N'-bis(ethylenesalicylidene)-ethane-1,2-diamine, N—N'-bis(ethylenesalicylidene)-propane-1,3-diamine, N—N'-bis(ethylenesalicylidene)-benzene-1,2-diamine, N—N'-bis(ethylenesalicylidene)-cyclohexane-1,2-diamine, N—N'-bis(3,5-di-tert-butyl ethylenesalicylidene)-ethane-1,2-diamine, N—N'-bis(3,5-di-methyl ethylenesalicylidene)-ethane-1,2-diamine, N—N'-bis(3-methyl ethylenesalicylidene)-ethane-1,2-diamine, N—N'-bis(5-methyl ethylenesalicylidene)-ethane-1,2-diamine, N—N'-bis(3-tert-butyl ethylenesalicylidene)-ethane-1,2-diamine, N—N'-bis(5-tert-butyl ethylenesalicylidene)-ethane-1,2-diamine, N—N'-bis(3-methyl, 5-tert-butyl ethylenesalicylidene)-ethane-1,2-diamine, N—N'-bis(3-tert-butyl, 5-methyl ethylenesalicylidene)-ethane-1,2-diamine, N—N'-bis(3-tert-butyl, 5-trifluoromethyl ethylenesalicylidene)-ethane-1,2-diamine, N—N'-bis(3-tert-butyl, 5-methoxy ethylenesalicylidene)-ethane-1,2-diamine, N—N'-bis(3-tert-butyl, 5-nitro ethylenesalicylidene)-ethane-1,2-diamine, N—N'-bis(3-tert-butyl, 5-chloro ethylenesalicylidene)-ethane-1,2-diamine, N—N'-bis(3-methyl, 5-trifluoromethyl ethylenesalicylidene)-ethane-1,2-diamine, N—N'-bis(3-methyl, 5-methoxy ethylenesalicylidene)-ethane-1,2-diamine, N—N'-bis(3-methyl, 5-nitro ethylenesalicylidene)-ethane-1,2-diamine, N—N'-bis(3-methyl, 5-chloro ethylenesalicylidene)-ethane-1,2-diamine, N—N'-bis(3,5-di-tert-butyl ethylenesalicylidene)-propane-1,3-diamine, N—N'-bis(3,5-di-methyl ethylenesalicylidene)-propane-1,3-diamine, N—N'-bis(3-methyl ethylenesalicylidene)-propane-1,3-diamine, N—N'-bis(5-methyl ethylenesalicylidene)-propane-1,3-diamine, N—N'-bis(3-tert-butyl ethylenesalicylidene)-propane-1,3-diamine, N—N'-bis(5-tert-butyl ethylenesalicylidene)-propane-1,3-diamine, N—N'-bis(3-methyl, 5-tert-butyl ethylenesalicylidene)-propane-1,3-diamine, N—N'-bis(3-tert-butyl, 5-methyl ethylenesalicylidene)-propane-1,3-diamine, N—N'-bis(3-tert-butyl, 5-trifluoromethyl ethylenesalicylidene)-propane-1,3-diamine, N—N'-bis(3-tert-butyl, 5-methoxy ethylenesalicylidene)-propane-1,3-diamine, N—N'-bis(3-tert-butyl, 5-nitro ethylenesalicylidene)-propane-1,3-diamine, N—N'-bis(3-tert-butyl, 5-chloro ethylenesalicylidene)-propane-1,3-diamine, N—N'-bis(3-methyl, 5-trifluoromethyl ethylenesalicylidene)-propane-1,3-diamine, N—N'-bis(3-methyl, 5-methoxy ethylenesalicylidene)-propane-1,3-diamine, N—N'-bis(3-methyl, 5-nitro ethylenesalicylidene)-propane-1,3-diamine, N—N'-bis(3-methyl, 5-chloro ethylenesalicylidene)-propane-1,3-diamine, N—N'-bis(3,5-di-tert-butyl ethylenesalicylidene)-benzene-1,2-diamine, N—N'-bis(3,5-di-methyl ethylenesalicylidene)-benzene-1,2-diamine, N—N'-bis(3-methyl ethylenesalicylidene)-benzene-1,2-diamine, N—N'-bis(5-methyl ethylenesalicylidene)-benzene-1,2-diamine, N—N'-bis(3-tert-butyl ethylenesalicylidene)-benzene-1,2-diamine, N—N'-bis(5-tert-butyl ethylenesalicylidene)-benzene-1,2-diamine, N—N'-bis(3-methyl, 5-tert-butyl ethylenesalicylidene)-benzene-1,2-diamine, N—N'-bis(3-tert-butyl, 5-methyl ethylenesalicylidene)-benzene-1,2-diamine, N—N'-bis(3-tert-butyl, 5-trifluoromethyl ethylenesalicylidene)-benzene-1,2-diamine, N—N'-bis(3-tert-butyl, 5-methoxy ethylenesalicylidene)-benzene-1,2-diamine, N—N'-bis(3-tert-butyl, 5-nitro ethylenesalicylidene)-benzene-1,2-diamine, N—N'-bis(3-tert-butyl, 5-chloro ethylenesalicylidene)-benzene-1,2-diamine, N—N'-bis(3-methyl, 5-trifluoromethyl ethylenesalicylidene)-benzene-1,2-diamine, N—N'-bis(3 methyl, 5-methoxy ethylenesalicylidene)-benzene-1,2-diamine, N—N'-bis(3-methyl, 5-nitro ethylenesalicylidene)-benzene-1,2-diamine, N—N'-bis(3-methyl, 5-chloro ethylenesalicylidene)-benzene-1,2-diamine, N—N'-bis(3,5-di-tert-butyl ethylenesalicylidene)-cyclohexane-1,2-diamine, N—N'-bis(3,5-di-methyl ethylenesalicylidene)-cyclohexane-1,2-diamine, N—N'-bis(3-methyl ethylenesalicylidene)-cyclohexane-1,2-diamine, N—N'-bis(5-methyl ethylenesalicylidene)-cyclohexane-1,2-diamine, N—N'-bis(3-tert-butyl ethylenesalicylidene)-cyclohexane-1,2-diamine, N—N'-bis(5-tert-butyl ethylenesalicylidene)-cyclohexane-1,2-diamine, N—N'-bis(3-methyl, 5-tert-butyl ethylenesalicylidene)-cyclohexane-1,2-diamine, N—N'-bis(3-tert-butyl, 5-methyl ethylenesalicylidene)-cyclohexane-1,2-diamine, N—N'-bis(3-tert-butyl, 5-trifluoromethyl ethylenesalicylidene)-cyclohexane-1,2-diamine, N—N'-bis(3-tert-butyl, 5-methoxy ethylenesalicylidene)-cyclohexane-1,2-diamine, N—N'-bis(3-tert-butyl, 5-nitro ethylenesalicylidene)-cyclohexane-1,2-diamine, N—N'-bis(3-tert-butyl, 5-chloro ethylenesalicylidene)-cyclohexane-1,2-diamine, N—N'-bis(3-methyl, 5-trifluoromethyl ethylenesalicylidene)-cyclohexane-1,2-diamine, N—N'-bis(3-methyl, 5-methoxy ethylenesalicylidene)-cyclohexane-1,2-diamine, N—N'-bis(3-methyl, 5-nitro ethylenesalicylidene)-cyclohexane-1,2-diamine, or N—N'-bis(3-methyl, 5-chloro ethylenesalicylidene)-cyclohexane-1,2-diamine.

In one aspect of the invention, the halohydrin agent in b) is the halogen compound selected from sodium iodide (NaI), sodium bromide (NaBr), sodium chloride (NaCl), potassium iodide (KI), potassium bromide (KBr), tetrabutylammonium iodide (TBAI), N-chlorosuccinimide (NCS), N-bromosuccinimide (NBS), N-iodosuccinimide (NIS), iodine ($I_2$), bromine ($Br_2$), or mixture thereof. Preferably, the halohydrin agent in b) is the halogen compound selected from N-bromosuccinimide.

In one aspect of the invention, the halohydrin agent in b) further comprises the oxidant selected from potassium persulfate ($K_2S_2O_8$), hydrogen peroxide ($H_2O_2$), tert-butyl hydroperoxide, calcium hypochlorite ($Ca(OCl)_2$), benzoyl peroxide, potassium nitrate ($KNO_3$), or mixture thereof.

In one aspect of the invention, at least one solvent is selected from, but not limited to water, acetone, dichloromethane, hexane, benzene, toluene, dimethylformamide, acetonitrile, or mixture thereof. Preferably, the solvent is the mixture of water and acetone.

In one aspect of the invention, at least one base is selected from potassium carbonate ($K_2CO_3$), sodium carbonate ($Na_2CO_3$), sodium bicarbonate ($NaHCO_3$), cesium carbonate ($Ce_2CO_3$), 1,8-diazabicyclo[5.4.0]undec-7-ene (DBU), or mixture thereof.

In one aspect of the invention, this invention relates to the process for cyclic carbonate production from $CO_2$ and olefins, comprising the contact of the catalyst composition as described above to the mixture of $CO_2$ and olefins In another aspect of the invention, this invention relates to the process for cyclic carbonate production from $CO_2$ and olefins, comprising the following steps:
  i) the contact of olefins to the halohydrin agent in at least one solvent; and
  ii) the contact of mixture obtained from step i), $CO_2$ and at least one base to the metal complex catalyst selected from the metal complex as described above.

In one aspect of the invention, the metal complex catalyst further comprises the organic compound as the co-catalyst selected from compound containing nitrogen, compound of quaternary ammonium salts, or compound of iminium salts.

In one aspect of the invention, the metal complex catalyst further comprises the organic compound as the co-catalyst selected from, but not limited to 4-dimethylaminopyridine (DMAP), tetrabutylammonium bromide (TBAB), tetrabutylammonium chloride (TBAC), tetrabutylammonium iodide (TBAI), imidazolium bromide, imidazolium chloride, imidazolium iodide, bis(triphenylphosphine) iminium bromide, bis(triphenylphosphine) iminium chloride, bis(triphenylphosphine) iminium iodide, or mixture thereof.

In one aspect of the invention, olefin is selected from ethylene, propylene, butylene, 1,4-butadiene, styrene, 1-hexene, or 1-octene. Preferably, olefin is ethylene.

In one aspect of the invention, the halohydrin agent in step i) is the halogen compound selected from sodium iodide (NaI), sodium bromide (NaBr), sodium chloride (NaCl), potassium iodide (KI), potassium bromide (KBr), tetrabutylammonium iodide (TBAI), N-chlorosuccinimide (NCS), N-bromosuccinimide (NBS), N-iodosuccinimide (NIS), iodine ($I_2$), bromine ($Br_2$), or mixture thereof. Preferably, the halohydrin agent in step i) is the halogen compound selected from N-bromosuccinimide.

In one aspect of the invention, the halohydrin agent in step i) further comprises the oxidant selected from potassium persulfate ($K_2S_2O_8$), hydrogen peroxide ($H_2O_2$), tert-butyl hydroperoxide, calcium hypochlorite ($Ca(OCl)_2$), benzoyl peroxide, potassium nitrate ($KNO_3$), or mixture thereof.

In one aspect of the invention, at least one solvent in step i) is selected from water, acetone, dichloromethane, hexane, benzene, toluene, dimethylformamide, acetonitrile, or mixture thereof. Preferably, the solvent in step i) is the mixture of water and acetone.

In one aspect of the invention, at least one base in step ii) is selected from potassium carbonate ($K_2CO_3$), sodium carbonate ($Na_2CO_3$), sodium bicarbonate ($NaHCO_3$), cesium carbonate ($Ce_2CO_3$), 1,8-diazabicyclo[5.4.0]undec-7-ene (DBU), or mixture thereof.

In one aspect of the invention, step ii) is operated under the presence of organic solvent selected from dichloromethane, hexane, benzene, toluene, dimethylformamide, or mixture thereof.

In one aspect of the invention, the temperature in step i) is in the range of 30 to 80° C. and the temperature in step ii) is in the range of 50 to 120° C.

In one aspect of the invention, the mole ratio of the metal complex to olefins is in the range of 1:10 to 1:10000 and the $CO_2$ pressure in step ii) is in the range of 15 to 600 psi.

The cyclic carbonate production from $CO_2$ and olefins according to this invention may further comprises the drying step if necessary, wherein said step may be selected from, but not limited to stir-drying or vacuum drying, etc.

In one aspect, the cyclic carbonate production from $CO_2$ and olefins according to this invention may be operated in the reactor, but not limited to fixed-bed reactor. The operation may be performed in batch or continuous manner.

The following examples are for demonstrating one aspect of the invention only and not intended to be limitation of the scope of this invention in any way.

Example 1: Synthesis of N—N'-bis(ethylenesalicylidene)-diamine Ligand and its Derivatives to be Used in the Synthesis of Metal Complex Catalyst Containing Said Ligand Synthesis of Ligand to be Used in the Synthesis of Catalyst A The solution of 7-hydroxy-1-indanone in ethanol at the concentration of 0.67 M was prepared by dissolving 0.30 g (2 mmol) of 7-hydroxy-1-indanone in 3 mL of ethanol. Then, the 1,2-ethylene diamine was added into said solution. The mole ratio of 7-hydroxy-1-indanone to 1,2-ethylene diamine was 2:1. After that, the acetic acid was added about 1-2 drops. The obtained mixture was stirred while heated until reflux for 48 hours. Then, the obtained mixture was filtered to separate the solid. The obtained solid was washed with 10 mL of diethyl ether for 3 times. The N—N'-bis(ethylenesalicylidene)-ethane-1,2-diamine ligand was obtained as yellow solid.

Synthesis of Ligand to be Used in the Synthesis of Catalyst B

The synthesis of ligand to be used in the synthesis of catalyst B was prepared by the same method as the synthesis of ligand to be used in the synthesis of catalyst A.

Synthesis of Ligand to be Used in the Synthesis of Catalyst C

The solution of 4,6-di-tert-butyl-7-hydroxy-2,3-dihydro-1-indanone in ethanol at the concentration of 0.67 M was prepared by dissolving 0.52 g (2 mmol) of 4,6-di-tert-butyl-7-hydroxy-2,3-dihydro-1-indanone in 3 mL of ethanol. Then, the 1,2-ethylene diamine was added into said solution. The mole ratio of 4,6-di-tert-butyl-7-hydroxy-2,3-dihydro-1-indanone to 1,2-ethylene diamine was 2:1. After that, the acetic acid was added about 1-2 drops. The obtained mixture was stirred while heated until reflux for 48 hours. Then, the obtained mixture was filtered to separate the solid. The obtained solid was washed with 10 mL of diethyl ether for 3 times. The N—N'-bis(3,5-di-tert-butyl ethylenesalicylidene)-ethane-1,2-diamine ligand was obtained as yellow solid.

Synthesis of Ligand to be Used in the Synthesis of Catalyst D

The solution of 7-hydroxy-1-indanone in ethanol at the concentration of 0.67 M was prepared by dissolving 0.30 g (2 mmol) of 7-hydroxy-1-indanone in 3 mL of ethanol. Then, the 1,2-phenylene diamine was added into said solution. The mole ratio of 7-hydroxy-1-indanone to 1,2-phenylene diamine was 2:1. After that, the acetic acid was added about 1-2 drops. The obtained mixture was stirred while heated until reflux for 48 hours. Then, the obtained mixture was filtered to separate the solid. The obtained solid was washed with 10 mL of diethyl ether for 3 times. The N—N'-bis(ethylenesalicylidene)-benzene-1,2-diamine ligand was obtained as yellow solid.

Example 2: Synthesis of Metal Complex Catalyst Containing N—N'-bis(ethylenesalicylidene)-Diamine Ligand and its Derivatives Synthesis of Catalyst A The solution of N—N'-bis(ethylenesalicylidene)-ethane-1,2-diamine ligand in toluene at the concentration of 0.062 M was prepared by dissolving 0.20 g (0.62 mmol) of N—N'-bis(ethylenesalicylidene)-ethane-1,2-diamine ligand in 10 mL of toluene. Then, 0.10 g (0.62 mmol) of iron (III) chloride ($FeCl_3$) and triethylamine were mixed, respectively. The mole ratio of N—N'-bis(ethylenesalicylidene)-ethane-1,2-diamine ligand to iron (III) chloride to triethylamine was 1:1:2. After that, the obtained mixture was stirred and heated at the temperature of 100° C. until reflux under nitrogen atmosphere for 12 hours. The obtained mixture was filtered through celite. Then, the obtained solution was evaporated under vacuum condition. The catalyst A was obtained as red-brown solid.

Synthesis of Catalyst B

The solution of N—N'-bis(ethylenesalicylidene)-ethane-1,2-diamine ligand in tetrahydrofuran at the concentration of 0.031 M was prepared by dissolving 0.10 g (0.31 mmol) of N—N'-bis(ethylenesalicylidene)-ethane-1,2-diamine ligand in 10 mL of tetrahydrofuran. Then, 0.015 g (0.62 mmol) of sodium hydride was mixed into said solution and stirred at room temperature for 1 hour. Then, the obtained mixture was mixed with 0.12 g (0.31 mmol) of chromium (III) chloride tetrahydrofuran ($CrCl_3$ $(THF)_3$). The mole ratio of N—N'-bis(ethylenesalicylidene)-ethane-1,2-diamine ligand to chromium (III) chloride tetrahydrofuran to sodium hydride was 1:1:2. After that, the obtained mixture was stirred at room temperature under nitrogen atmosphere for 12 hours. The obtained mixture was filtered. The obtained solid was washed with saturated sodium chloride solution and water, respectively. Then, the obtained solid was evaporated under vacuum condition. The catalyst B was obtained as light brown solid.

Synthesis of Catalyst C

The solution of N—N'-bis(3,5-di-tert-butyl ethylenesalicylidene)-ethane-1,2-diamine ligand in tetrahydrofuran at the concentration of 0.018 M was prepared by dissolving 0.10 g (0.18 mmol) of N—N'-bis(3,5-di-tert-butyl ethylenesalicylidene)-ethane-1,2-diamine ligand in 10 mL of tetrahydrofuran. Then, 0.0088 g (0.37 mmol) of sodium hydride was mixed into said solution and stirred at room temperature for 1 hour. Then, the obtained mixture was mixed with 0.068 g (0.18 mmol) of chromium (III) chloride tetrahydrofuran ($CrCl_3$ $(THF)_3$). The mole ratio of N—N'-bis(3,5-di-tert-butyl ethylenesalicylidene)-ethane-1,2-diamine ligand to chromium (III) chloride tetrahydrofuran to sodium hydride was 1:1:2. After that, the obtained mixture was stirred at room temperature under nitrogen atmosphere for 12 hours. The obtained mixture was filtered. The obtained solid was washed with saturated sodium chloride solution and water, respectively. Then, the obtained solid was evaporated under vacuum condition. The catalyst C was obtained as light brown solid.

Synthesis of Catalyst D

The solution of N—N'-bis(ethylenesalicylidene)-benzene-1,2-diamine ligand in tetrahydrofuran at the concentration of 0.027 M was prepared by dissolving 0.10 g (0.27 mmol) of N—N'-bis(ethylenesalicylidene)-benzene-1,2-diamine ligand in 10 mL of tetrahydrofuran. Then, 0.013 g (0.54 mmol) of sodium hydride was mixed into said solution and stirred at room temperature for 1 hour. Then, the obtained mixture was mixed with 0.10 g (0.27 mmol) of chromium (III) chloride tetrahydrofuran (CrCl$_3$ (THF)$_3$). The mole ratio of N—N'-bis(ethylenesalicylidene)-benzene-1,2-diamine ligand to chromium (III) chloride tetrahydrofuran to sodium hydride was 1:1:2. After that, the obtained mixture was stirred at room temperature under nitrogen atmosphere for 12 hours. The obtained mixture was filtered. The obtained solid was washed with saturated sodium chloride solution and water, respectively. Then, the obtained solid was evaporated under vacuum condition. The catalyst D was obtained as light brown solid.

Example 3: Preparation of Cyclic Carbonate from the Reaction Between CO$_2$ and Olefins The metal complex catalyst containing N—N'-bis(ethylenesalicylidene)-diamine ligand and its derivatives according to the invention which are catalyst A, B, C, and D will be tested for the ability in cyclic carbonate production from the reaction between CO$_2$ and olefins as follows:

Testing for the Ability in Cyclic Carbonate Production of the Catalyst According to the Invention Under the Condition of Halogen Compound as Halohydrin Agent and Further Comprising Oxidant Testing for the ability in cyclic carbonate production of the metal complex catalyst containing N—N'-bis(ethylenesalicylidene)-diamine ligand and its derivatives according to the invention under the condition of halogen compound as halohydrin agent and further comprising oxidant can be performed according to the following steps.

Step i):

1 mmol of olefins, 1 mmol of halogen compound which was sodium iodide or sodium bromide, 1 mmol of oxidant which was potassium persulfate, and 2 mL of water solvent were added into the reactor. The reactor was heated at the temperature of 60° C. for 2 to 5 hours; and Step ii):

About 4.06-7.30 mg of metal complex catalyst, 1.30 mg of organic compound as the co-catalyst which was 4-dimethylaminopyridine, 1 mmol of base which was potassium carbonate, and 2 mL of organic solvent which was dimethylformamide were added into the reactor containing the mixture from step i). Then, carbon dioxide gas was added into the reactor at the pressure of 300 psi. The reactor was heated at the temperature of 60° C. for 1 to 5 hours. After the reaction time was reached, the temperature of the reactor was reduced to the room temperature. The obtained product was cyclic carbonate which would be identified by NMR spectrometry technique.

Testing for the Ability in Cyclic Carbonate Production of the Catalyst According to the Invention Under the Condition of Halogen Compound as Halohydrin Agent Testing for the ability in cyclic carbonate production of the metal complex catalyst containing N—N'-bis(ethylenesalicylidene)-diamine ligand and its derivatives according to the invention under the condition of halogen compound as halohydrin agent can be performed according to the following steps.

Step i):

1 mmol of olefins, 1 mmol of halogen compound which was N-Bromosuccinimide (NBS), 2 mL of acetone solvent, and 2 mL of water solvent were added into the reactor. The reactor was heated at the temperature of 40° C. for 2 hours; and Step ii):

About 4.06-7.30 mg of metal complex catalyst, 1.30 mg of organic compound as the co-catalyst which was 4-dimethylaminopyridine, and 1 mmol of base which was potassium carbonate were added into the reactor containing the mixture from step i). Then, carbon dioxide gas was added into the reactor at the pressure of 300 psi. The reactor was heated at the temperature of 60° C. for 2 hours. After the reaction time was reached, the temperature of the reactor was reduced to the room temperature. The obtained product was cyclic carbonate which would be identified by NMR spectrometry technique.

Testing for the Ability in One Step Cyclic Carbonate Production of the Catalyst According to the Invention Under the Condition of Halogen Compound as Halohydrin Agent and Further Comprising Oxidant Testing for the ability in one step cyclic carbonate production of the metal complex catalyst containing N—N'-bis(ethylenesalicylidene)-diamine ligand and its derivatives according to the invention under the condition of halogen compound as halohydrin agent and further comprising oxidant can be performed according to the following steps.

1 mmol of olefins, 1 mmol of halogen compound which was sodium iodide, 1 mmol of oxidant which was potassium persulfate, 2 mL of water solvent, 1 mL of dimethylformamide solvent, 1 mmol of base which was potassium carbonate, and about 4.06-7.30 mg of metal complex catalyst including 1.30 mg of organic compound as the co-catalyst which was 4-dimethylaminopyridine were added into the reactor. Then, carbon dioxide gas was added into the reactor at the pressure of 300 psi. The reactor was heated at the temperature of 60° C. for 10 hours. After the reaction time was reached, the temperature of the reactor was reduced to the room temperature. The obtained product was cyclic carbonate which would be identified by NMR spectrometry technique.

Structure of the Catalyst According to the Invention

The structure of the synthesized metal complex catalyst containing N—N'-bis(ethylenesalicylidene)-diamine ligand and its derivatives is shown in table 1.

TABLE 1

Structure of the metal complex catalyst containing N-N'-bis(ethylenesalicylidene)-diamine ligand and its derivatives according to the invention

| Sample | Name | Structure |
|---|---|---|
| Catalyst A | N-N'-bis(ethylenesalicylidene)-ethane-1,2-diaminoiron (III) chloride | 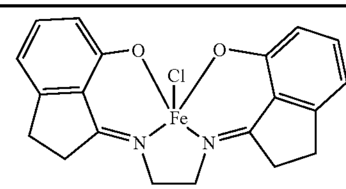 |

TABLE 1-continued

Structure of the metal complex catalyst containing N-N'-bis(ethylenesalicylidene)-diamine ligand and its derivatives according to the invention

| Sample | Name | Structure |
|---|---|---|
| Catalyst B | N-N'-bis(ethylenesalicylidene)-ethane-1,2-diaminochromium (III) chloride | (structure) |
| Catalyst C | N-N'-bis(3,5-di-tert-butyl ethylenesalicylidene)-ethane-1,2-diaminochromium (III) chloride | (structure) |
| Catalyst D | N-N'-bis(ethylenesalicylidene)-benzene-1,2-diaminochromium (III) chloride | (structure) |

Cyclic Carbonate Formation

The catalytic ability for the cyclic carbonate formation from $CO_2$ and olefins of the metal complex catalyst containing N—N'-bis(ethylenesalicylidene)-diamine ligand and its derivatives according to the invention which are catalyst A, B, C, and D comparing to the non-catalytic conditions is shown in table 2 and 3.

TABLE 2

Catalytic ability for the cyclic carbonate formation of the metal complex catalyst containing N-N'-bis(ethylenesalicylidene)-diamine ligand and its derivatives according to the invention

| Metal complex catalyst | Olefins | Halohydrin agent | Mole ratio of catalyst: co-catalyst: olefins | Time for step i) (hr) | Time for step ii) (hr) | % Conversion of olefins | % Yield of cyclic carbonate |
|---|---|---|---|---|---|---|---|
| None | styrene | NaI/$K_2S_2O_8$ | 0:1:100 | 2 | 4 | 96 | 39 |
| A | styrene | NaI/$K_2S_2O_8$ | 1:1:100 | 2 | 4 | 91 | 58 |
| B | styrene | NaI/$K_2S_2O_8$ | 1:1:100 | 2 | 4 | 89 | 65 |
| B | styrene | NaI/$K_2S_2O_8$ | 1:1:100 | 2 | 1 | 82 | 66 |
| B | styrene | NaI/$K_2S_2O_8$ | 1:1:100 | 2 | 2 | 86 | 77 |
| C | styrene | NaI/$K_2S_2O_8$ | 1:1:100 | 2 | 2 | 86 | 59 |
| D | styrene | NaI/$K_2S_2O_8$ | 1:1:100 | 2 | 2 | 95 | 87 |
| D | 1-hexene | NaI/$K_2S_2O_8$ | 1:1:100 | 2 | 2 | 96 | 85 |
| B | styrene | NaBr/$K_2S_2O_8$ | 1:1:100 | 5 | 5 | 87 | 77 |
| B | 1-hexene | NaBr/$K_2S_2O_8$ | 1:1:100 | 5 | 5 | 100 | 94 |
| D | styrene | NBS | 1:1:100 | 2 | 2 | 100 | 96 |
| D | 1-hexene | NBS | 1:1:100 | 2 | 2 | 100 | 88 |
| D | styrene | NBS | 1:0:100 | 2 | 2 | 100 | 95 |
| D[a] | styrene | NBS | 1:0:200 | 2 | 2 | 100 | 87 |
| D[b] | styrene | NBS | 1:0:1000 | 2 | 2 | 100 | 83 |
| D | 1-hexene | NBS | 1:0:100 | 2 | 2 | 100 | 87 |
| D | 1-octene | NBS | 1:0:100 | 2 | 2 | 100 | 85 |
| D | 1,4-butadiene | NBS | 1:0:100 | 2 | 2 | 100 | 97 |
| D | ethylene | NBS | 1:0:100 | 2 | 2 | 100 | 100 |

[a] amount of metal complex catalyst 0.5% mole
[b] amount of metal complex catalyst 0.1% mole

TABLE 3

Catalytic ability for the cyclic carbonate formation of the metal complex catalyst containing N-N'-bis(ethylenesalicylidene)-diamine ligand and its derivatives according to the invention

| Metal complex catalyst | Olefins | Halohydrin agent | Mole ratio of catalyst:co-catalyst:olefins | % Conversion of olefins | % Yield of cyclic carbonate |
|---|---|---|---|---|---|
| None | styrene | NaBr/$K_2S_2O_8$ | 0:1:100 | 95 | 49 |
| B | styrene | NaBr/$K_2S_2O_8$ | 1:1:100 | 91 | 57 |
| None | styrene | NaI/$K_2S_2O_8$ | 0:1:100 | 71 | 58 |
| B | styrene | NaI/$K_2S_2O_8$ | 1:1:100 | 90 | 84 |
| B | 1-hexene | NaI/$K_2S_2O_8$ | 1:1:100 | 100 | 84 |

BEST MODE OR PREFERRED EMBODIMENT OF THE INVENTION

Best mode or preferred embodiment of the invention is as provided in the description of the invention.

The invention claimed is:

1. A catalyst composition for cyclic carbonate production from $CO_2$ and olefins, wherein said catalyst composition comprises:
   a) the metal complex as shown in structure (I):

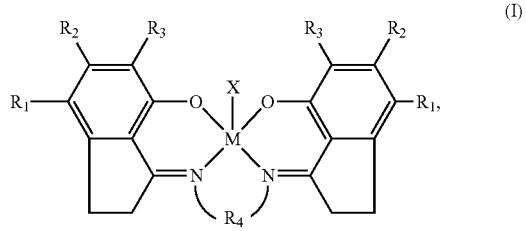

wherein,
   M represents transition metal atom;
   $R_1$, $R_2$, and $R_3$ represent independent group selected from hydrogen atom, halogen atom, alkyl group, alkenyl group, alkynyl group, alkoxy group, amine group, phenyl group, benzyl group, cyclic hydrocarbon group comprising hetero atom, perfluoroalkyl group, or nitro group;
   $R_4$ represents group selected from alkylene group, cycloalkylene group, or phenylene group;
   X represents group selected from halogen atom, acetate group, or triflate group;
   b) the halohydrin agent in at least one solvent; and
   c) at least one base.

2. The catalyst composition according to claim 1, wherein in the metal complex in a), M represents transition metal atom selected from chromium, cobalt, or iron.

3. The catalyst composition according to claim 2, wherein in the metal complex in a), M is chromium metal atom.

4. The catalyst composition according to claim 1, wherein in the metal complex in a), $R_1$, $R_2$, and $R_3$ represent independent group selected from hydrogen atom, halogen atom, alkyl group having 1 to 4 carbon atoms, alkenyl group having 1 to 4 carbon atoms, alkynyl group having 1 to 4 carbon atoms, alkoxy group having 1 to 4 carbon atoms, amine group, phenyl group, benzyl group, cyclic hydrocarbon group comprising hetero atom, perfluoroalkyl group, or nitro group.

5. The catalyst composition according to claim 1 or 4, wherein in the metal complex in a), $R_1$, $R_2$, and $R_3$ represent independent group selected from hydrogen atom, chlorine atom, methyl group, ethyl group, iso-propyl group, n-butyl group, tert-butyl group, methoxy group, ethoxy group, iso-propoxy group, n-butoxy group, tert-butoxy group, phenyl group, benzyl group, trifluoromethyl group, or nitro group.

6. The catalyst composition according to claim 5, wherein in the metal complex in a), $R_1$, $R_2$, and $R_3$ are hydrogen atom.

7. The catalyst composition according to claim 1, wherein in the metal complex in a), $R_4$ represents group selected from alkylene group having 2 to 3 carbon atoms, cycloalkylene group having 6 carbon atoms, or phenylene group.

8. The catalyst composition according to claim 1 or 7, wherein in the metal complex in a), $R_4$ represents group selected from ethylene group, 1,3-propylene group, 1,2-cyclohexylene group, or 1,2-phenylene group.

9. The catalyst composition according to claim 8, wherein in the metal complex in a), $R_4$ is 1,2-phenylene group.

10. The catalyst composition according to claim 1, wherein in the metal complex in a), X represents group selected from chlorine atom, bromine atom, iodine atom, acetate group, or triflate group.

11. The catalyst composition according to claim 1, wherein the metal complex in a) is selected from N—N'-bis(ethylenesalicylidene)-ethane-1,2-diamino metal (III) chloride, N—N'-bis(ethylenesalicylidene)-propane-1,3-diamino metal (III) chloride, N—N'-bis(ethylenesalicylidene)-benzene-1,2-diamino metal (III) chloride, N—N'-bis(ethylenesalicylidene)-cyclohexane-1,2-diamino metal (III) chloride, N—N'-bis(3,5-di-tert-butyl ethylenesalicylidene)-ethane-1,2-diamino metal (III) chloride, N—N'-bis(3,5-dimethyl ethylenesalicylidene)-ethane-1,2-diamino metal (III) chloride, N—N'-bis(3-methyl ethylenesalicylidene)-ethane-1,2-diamino metal (III) chloride, N—N'-bis(5-methyl ethylenesalicylidene)-ethane-1,2-diamino metal (III) chloride, N—N'-bis(3-tert-butyl ethylenesalicylidene)-ethane-1,2-diamino metal (III) chloride, N—N'-bis(5-tert-butyl ethylenesalicylidene)-ethane-1,2-diamino metal (III) chloride, N—N'-bis(3-methyl, 5-tert-butyl ethylenesalicylidene)-ethane-1,2-diamino metal (III) chloride, N—N'-bis(3-tert-butyl, 5-methyl ethylenesalicylidene)-ethane-1,2-diamino metal (III) chloride, N—N'-bis(3-tert-butyl, 5-trifluoromethyl ethylenesalicylidene)-ethane-1,2-diamino metal (III) chloride, N—N'-bis(3-tert-butyl, 5-methoxy ethylenesalicylidene)-ethane-1,2-diamino metal (III) chloride, N—N'-bis(3-tert-butyl, 5-nitro ethylenesalicylidene)-ethane-1,2-diamino metal (III) chloride, N—N'-bis(3-tert-butyl, 5-chloro ethylenesalicylidene)-ethane-1,2-diamino metal (III) chloride, N—N'-bis(3-methyl, 5-trifluoromethyl ethylenesalicylidene)-ethane-1,2-diamino metal (III) chloride, N—N'-bis(3-methyl, 5-methoxy ethylenesalicylidene)-ethane-1,2-diamino metal (III) chloride, N—N'-bis(3-methyl, 5-nitro ethylenesalicylidene)-ethane-1,2-diamino metal (III) chloride, N—N'-bis(3-methyl, 5-chloro ethylenesalicylidene)-ethane-1,2-diamino metal (III) chloride, N—N'-bis(3,5-di-tert-butyl ethylenesalicylidene)-propane-1,3-diamino metal (III) chloride, N—N'-bis(3,5-di-methyl ethylenesalicylidene)-propane-1,3-diamino metal (III) chloride, N—N'-bis(3-methyl ethylenesalicylidene)-propane-1,3-diamino metal (III) chloride, N—N'-bis(5-methyl ethylenesalicylidene)-propane-1,3-diamino metal (III) chloride, N—N'-bis(3-tert-butyl ethylenesalicylidene)-propane-1,3-diamino metal (III) chloride, N—N'-bis(5-tert-butyl ethylenesalicylidene)-propane-1,3-diamino metal (III) chloride, N—N'-bis(3-methyl, 5-tert-butyl ethylenesalicylidene)-propane-1,3-diamino metal (III) chloride, N—N'-bis(3-tert-butyl, 5-methyl ethylenesalicylidene)-propane-1,3-diamino metal (III) chloride, N—N'-bis(3-tert-butyl, 5-trifluoromethyl ethylenesalicylidene)-propane-1,3-diamino metal (III) chloride, N—N'-bis(3-tert-butyl, 5-methoxy ethylenesalicylidene)-propane-1,3-diamino metal (III) chloride, N—N'-bis(3-tert-butyl, 5-nitro ethylenesalicylidene)-propane-1,3-diamino metal (III) chloride, N—N'-bis(3-tert-butyl, 5-chloro ethylenesalicylidene)-propane-1,3-diamino metal (III) chloride, N—N'-bis(3-methyl, 5-trifluoromethyl ethylenesalicylidene)-propane-1,3-diamino metal (III) chloride, N—N'-bis(3-methyl, 5-methoxy ethylenesalicylidene)-propane-1,3-diamino metal (III) chloride, N—N'-bis(3-methyl, 5-nitro ethylenesalicylidene)-propane-1,3-diamino metal (III) chloride, N—N'-bis(3-methyl, 5-chloro ethylenesalicylidene)-propane-1,3-diamino metal (III) chloride, N—N'-bis(3,5-di-tert-butyl ethylenesalicylidene)-benzene-1,2-diamino metal (III) chloride, N—N'-bis(3,5-di-methyl ethylenesalicylidene)-benzene-1,2-diamino metal (III) chloride, N—N'-bis(3-methyl ethylenesalicylidene)-benzene-1,2-diamino metal (III) chloride, N—N'-bis(5-methyl ethylenesalicylidene)-benzene-1,2-diamino metal (III) chloride, N—N'-bis(3-tert-butyl ethylenesalicylidene)-benzene-1,2-diamino metal (III) chloride, N—N'-bis(5-tert-butyl ethylenesalicylidene)-benzene-1,2-diamino metal (III) chloride, N—N'-bis(3-methyl, 5-tert-butyl ethylenesalicylidene)-benzene-1,2-diamino metal (III) chloride, N—N'-bis(3-tert-butyl, 5-methyl ethylenesalicylidene)-benzene-1,2-diamino metal (III) chloride, N—N'-bis(3-tert-butyl, 5-trifluoromethyl ethylenesalicylidene)-benzene-1,2-diamino metal (III) chloride, N—N'-bis(3-tert-butyl, 5-methoxy ethylenesalicylidene)-benzene-1,2-diamino metal (III) chloride, N—N'-bis(3-tert-butyl, 5-nitro ethylenesalicylidene)-benzene-1,2-diamino metal (III) chloride, N—N'-bis(3-tert-butyl, 5-chloro ethylenesalicylidene)-benzene-1,2-diamino metal (III) chloride, N—N'-bis(3-methyl, 5-trifluoromethyl ethylenesalicylidene)-benzene-1,2-diamino metal (III) chloride, N—N'-bis(3-methyl, 5-methoxy ethylenesalicylidene)-benzene-1,2-diamino metal (III) chloride, N—N'-bis(3-methyl, 5-nitro ethylenesalicylidene)-benzene-1,2-diamino metal (III) chloride, N—N'-bis(3-methyl, 5-chloro ethylenesalicylidene)-benzene-1,2-diamino metal (III) chloride, N—N'-bis(3,5-di-tert-butyl ethylenesalicylidene)-cyclohexane-1,2-diamino metal (III) chloride, N—N'-bis(3,5-di-methyl ethylenesalicylidene)-cyclohexane-1,2-diamino metal (III) chloride, N—N'-bis(3-methyl ethylenesalicylidene)-cyclohexane-1,2-diamino metal (III) chloride, N—N'-bis(5-methyl ethylenesalicylidene)-cyclohexane-1,2-diamino metal (III) chloride, N—N'-bis(3-tert-butyl ethylenesalicylidene)-cyclohexane-1,2-diamino metal (III) chloride, N—N'-bis(5-tert-butyl ethylenesalicylidene)-cyclohexane-1,2-diamino metal (III) chloride, N—N'-bis(3-methyl, 5-tert-butyl ethylenesalicylidene)-cyclohexane-1,2-diamino metal (III) chloride, N—N'-bis(3-tert-butyl, 5-methyl ethylenesalicylidene)-cyclohexane-1,2-diamino metal (III) chloride, N—N'-bis(3-tert-butyl, 5-trifluoromethyl ethylenesalicylidene)-cyclohexane-1,2-diamino metal (III) chloride, N—N'-bis(3-tert-butyl, 5-methoxy ethylenesalicylidene)-cyclohexane-1,2-diamino metal (III) chloride, N—N'-bis(3-tert-butyl, 5-nitro ethylenesalicylidene)-cyclohexane-1,2-diamino metal (III) chloride, N—N'-bis(3-tert-butyl, 5-chloro ethylenesalicylidene)-cyclohexane-1,2-diamino metal (III) chloride, N—N'-bis(3-methyl, 5-trifluoromethyl ethylenesalicylidene)-cyclohexane-1,2-diamino metal (III) chloride, N—N'-bis(3-methyl, 5-methoxy ethylenesalicylidene)-cyclohexane-1,2-diamino metal (III) chloride, N—N'-bis(3-methyl, 5-nitro ethylenesalicylidene)-cyclohexane-1,2-diamino metal (III) chloride, or N—N'-bis(3-methyl, 5-chloro ethylenesalicylidene)-cyclohexane-1,2-diamino metal (III) chloride.

12. The catalyst composition according to claim 1, wherein the halohydrin agent in b) is the halogen compound.

13. The catalyst composition according to claim 12, wherein the halogen compound is selected from sodium iodide (NaI), sodium bromide (NaBr), sodium chloride (NaCl), potassium iodide (KI), potassium bromide (KBr), tetrabutylammonium iodide (TBAI), N-chlorosuccinimide (NCS), N-bromosuccinimide (NBS), N-iodosuccinimide (NIS), iodine ($I_2$), bromine ($Br_2$), or mixture thereof.

14. The catalyst composition according to claim 12 or 13, wherein the halogen compound is N-bromosuccinimide.

15. The catalyst composition according to claim 1 or 12, wherein the halohydrin agent in b) further comprises the oxidant selected from potassium persulfate ($K_2S_2O_8$), hydrogen peroxide ($H_2O_2$), tert-butyl hydroperoxide, calcium hypochlorite ($Ca(OCl)_2$), benzoyl peroxide, potassium nitrate ($KNO_3$), or mixture thereof.

16. The catalyst composition according to claim 1, wherein at least one solvent is selected from water, acetone, dichloromethane, hexane, benzene, toluene, dimethylformamide, acetonitrile, or mixture thereof.

17. The catalyst composition according to claim 16, wherein the solvent is the mixture of water and acetone.

18. The catalyst composition according to claim 1, wherein at least one base is selected from potassium carbonate ($K_2CO_3$), sodium carbonate ($Na_2CO_3$), sodium bicarbonate ($NaHCO_3$), cesium carbonate ($Ce_2CO_3$), 1,8-diazabicyclo[5.4.0]undec-7-ene (DBU), or mixture thereof.

* * * * *